(12) United States Patent
Weiss et al.

(10) Patent No.: US 9,205,250 B2
(45) Date of Patent: *Dec. 8, 2015

(54) SIGNAL LINE OF AN IMPLANTABLE ELECTROMEDICAL CONFIGURATION

(75) Inventors: Ingo Weiss, Berlin (DE); Stefan Knorr, Berlin (DE)

(73) Assignee: BIOTRONIK CRM Patent AG (CH)

( * ) Notice: Subject to any disclaimer, the term of this patent is extended or adjusted under 35 U.S.C. 154(b) by 1416 days.

This patent is subject to a terminal disclaimer.

(21) Appl. No.: 12/403,404

(22) Filed: Mar. 13, 2009

(65) Prior Publication Data

US 2009/0248102 A1 Oct. 1, 2009

(30) Foreign Application Priority Data

Mar. 29, 2008 (DE) .......................... 10 2008 016 364

(51) Int. Cl.
| | | |
|---|---|---|
| *A61N 1/08* | (2006.01) | |
| *A61N 1/05* | (2006.01) | |
| *A61N 1/02* | (2006.01) | |
| *H01L 41/04* | (2006.01) | |
| *A61N 1/378* | (2006.01) | |

(52) U.S. Cl.
CPC *A61N 1/05* (2013.01); *A61N 1/025* (2013.01); *H01L 41/044* (2013.01); *A61N 1/0541* (2013.01); *A61N 1/0563* (2013.01); *A61N 1/378* (2013.01); *A61N 2001/086* (2013.01)

(58) Field of Classification Search
CPC ..... A61N 1/05; A61N 1/08; A61N 2001/086; A61N 2001/32; A61N 2001/36; A61N 2001/3605; A61N 2001/36125; A61N 2001/36196; A61N 2001/3718; A61N 2001/375; A61N 2001/3752; A61N 2001/3754; A61B 5/0093; A61B 5/0095; A61B 5/0097; A61B 5/0048–5/0057; A61B 5/22–5/228
USPC .......................... 607/32, 37, 63, 76, 115, 116
See application file for complete search history.

(56) References Cited

U.S. PATENT DOCUMENTS

| | | | | |
|---|---|---|---|---|
| 5,065,083 | A * | 11/1991 | Owens .......................... | 320/127 |
| 5,314,448 | A * | 5/1994 | Kroll et al. ...................... | 607/5 |
| 5,411,535 | A * | 5/1995 | Fujii et al. ....................... | 607/32 |
| 5,749,909 | A * | 5/1998 | Schroeppel et al. ............ | 607/33 |
| 5,814,089 | A * | 9/1998 | Stokes et al. ..................... | 607/32 |
| 5,999,848 | A * | 12/1999 | Gord et al. ......................... | 607/2 |
| 6,141,588 | A * | 10/2000 | Cox et al. ........................... | 607/9 |
| 6,529,777 | B1 | 3/2003 | Holmstrom et al. | |
| 6,654,638 | B1 | 11/2003 | Sweeney | |
| 6,707,235 | B1 * | 3/2004 | Brebøl .......................... | 310/369 |
| 7,203,551 | B2 * | 4/2007 | Houben et al. ................ | 607/116 |
| 2003/0204140 | A1 * | 10/2003 | Ferek-Patric et al. ......... | 600/439 |
| 2004/0215243 | A1 * | 10/2004 | Houben et al. .................... | 607/5 |

(Continued)

FOREIGN PATENT DOCUMENTS

| | | |
|---|---|---|
| WO | WO 99/42169 A1 | 8/1999 |
| WO | WO 01/76687 A2 | 10/2001 |
| WO | WO 2005/093976 A1 | 10/2005 |

*Primary Examiner* — Carl H Layno
*Assistant Examiner* — Eugene Wu
(74) *Attorney, Agent, or Firm* — Craig A. Fieschko, Esq.; DeWitt Ross & Stevens S.C.

(57) ABSTRACT

A signal line for an implantable electromedical configuration, having an electric line segment or line end and a mechano-electric converter for converting an electric AC voltage signal into a mechanical oscillation. The oscillation can in turn be converted back into an electrical signal for delivery to a part of a human or mammal body, e.g., a heart.

13 Claims, 3 Drawing Sheets

(56) References Cited

U.S. PATENT DOCUMENTS

| | | | |
|---|---|---|---|
| 2004/0215279 A1* | 10/2004 | Houben et al. | 607/35 |
| 2005/0107831 A1* | 5/2005 | Hill et al. | 607/2 |
| 2006/0009818 A1* | 1/2006 | Von Arx et al. | 607/60 |
| 2007/0185549 A1* | 8/2007 | Zdeblick | 607/60 |
| 2008/0108915 A1* | 5/2008 | Penner | 601/2 |

* cited by examiner $U_{in}/U_{out} = l2/h$

SIGNAL LINE OF AN IMPLANTABLE ELECTROMEDICAL CONFIGURATION

FIELD OF THE INVENTION

The invention relates to a signal line of an implantable electromedical configuration for functional connection of a basic device (e.g., a heart pacemaker) to a sensor or actuator at a distance from the basic device (e.g., heart status sensor electrodes or stimulation electrodes).

BACKGROUND OF THE INVENTION

In the following discussion, it is largely assumed that both the basic device and the sensor and/or actuator are implantable, and that in the in-use state they are in fact implanted in the body of a living creature, in particular a human or some other mammal. However, the invention is fundamentally also implantable in other types of electric measurement and/or action configurations.

One configuration of the type in question that has been known for decades and has become extremely widespread is the heart pacemaker configuration consisting of a heart pacemaker as the basic device, with at least one electrode line connected to it as the signal line, with at least one electrode provided on the distal end of the signal line and placed in or on a patient's heart in the in-use state. However, devices of this type also include implantable defibrillators, stimulation configurations for stimulation of the cochlear nerve, or implantable measurement and transmission configurations for intracorporeal detection and analysis and/or external transmission of measured values of physiological variables. Such arrangements may use multiple actuators and/or sensors, for example, as in the case of pacemaker configurations with sensor electrodes and/or other sensors, e.g., for detecting the blood oxygen saturation or the internal vascular blood pressure.

With such configurations, the signal line is typically an electric line having at least one elongated electric conductor, usually structured in the form of a coil and/or cable. In configurations having multiple actuators and/or sensors, the basic device is connected to each actuator and/or sensor by a separate conductor wire which has sufficient insulation. Such signal lines are available in a variety of forms and have proven successful in a variety of applications for many decades. However, they are relatively thick and rigid, and they have susceptibility to interference due to external electromagnetic fields, when they comprise multiple separate conductors.

SUMMARY OF THE INVENTION

An object of the present invention is to provide an improved signal line of the type in question whose basic design offers the possibility of a thinner and less rigid structural embodiment, and an increase in interference resistance with respect to external fields.

This object may be achieved by a single line having features set forth in at least some of the accompanying claims. In addition, an implantable electrostimulation configuration with such a signal line is also proposed.

The invention is based on the idea of departing from the concept of continuous electric signal transmission between the basic device and connected peripheral devices, e.g., sensors and/or actuators. It includes the fundamental idea of providing means for electromechanical signal conversion in the signal line and, in preferred embodiments, also providing means for mechanoelectric conversion in order to convert first an electric AC voltage signal (received by normal input) into a mechanical oscillation via electromechanical signal conversion, and in the preferred embodiments also accomplishing a conversion back into an electric signal via mechanoelectric conversion. This signal conversion and, in another preferred embodiment, the fact that a mechanical segment is provided in the signal path lead to possibilities for achieving the desired improvements with respect to traditional, purely electric signal lines, which are explained in brief terms below in conjunction with embodiments of the invention.

In one embodiment of the invention, a mechanoelectric converter is connected following the electromechanical converter, such that the two converters form an AC voltage converter when connected in series, and such that a higher-resistance line segment is provided on an input end of the AC voltage converter in comparison with an output end. This higher-resistance line segment is less susceptible to electromagnetic interference (EMI) than, for example, the relatively low-resistance conductors of electrode lines used in the previous pacemaker technology. Providing a higher-resistance conductor with comparable line losses is made possible by use of the electromechanical and mechanoelectric converters, such that a higher voltage is fed into the line at the input of the AC voltage converter ("transformer") than is supplied at the output end.

In some versions of the invention, it is useful to provide an electric DC voltage on the actuator. For such applications, a rectifier unit, in particular one that is active, is connected following the mechanoelectric converter on its electric end and/or following the AC voltage converter on its output end.

In one preferred embodiment that can be implemented in an inexpensive and space-saving manner, at least one mechanoelectric converter and/or electromechanical converter has a piezoelectric element. Miniaturized piezoelectric elements are in use in many fields of technology and have achieved a high level of development which allows their use in this embodiment of the invention without significant additional development effort. Depending on the specific embodiment of the invention, it is possible to rely on various available design embodiments of individual piezoelectric elements, or those used in certain serial or parallel circuitry groups.

In one version of this embodiment, the AC voltage converter has a combination piezoelectric element that is provided with electrodes on two opposing surfaces and one surface perpendicular to the former and acts as a 3-point transformer. In another expedient embodiment, the AC voltage converter has a stack configuration of piezoelectric elements that act as a 4-point transformer.

More extensive utilization of the practical potential of the invention is possible with multiple mechanoelectric converters for providing multiple output voltages independently, namely in this case when a mechanoelectric converter is connected following each electromechanical converter, such that multiple independent AC voltage converters are provided in the signal line for parallel conversion of multiple input voltages that are supplied by the basic device or a sensor configuration into multiple output voltages can be transformed up separately for transmission on the electric line segment.

This design of the invention is embodied in an especially advantageous manner by the fact that the multiple AC voltage converters are connected to a shared feeder line on the input end or outgoing line or electrodes on the output end and means for frequency coding of the input and/or output voltage are provided. This makes it possible to significantly reduce the number of line wires in an electrode line or a similar signal cable—down to a single line wire in the ideal case. This also allows implementation of much thinner and more flexible connecting lines, which are therefore much less expensive.

A further simplification of the design of an electrode line of an electrostimulation device in particular can be achieved if the multiple AC voltage converters are each connected at one of their outputs to a common reference electrode and at one of their other outputs to a separate electrode. This reduces the number of electrodes at the surface of the electrode line and also reduces the structural complexity for the corresponding insulation.

As already indicated above, a simulation and/or sensing electrode line of an electrostimulation device, in particular a heart pacemaker, implantable defibrillator or cochlear nerve stimulator constitutes an especially important practical application of the invention.

From the standpoint of the configuration, there are other possibilities for simplification and cost reduction in addition to those mentioned above. First, at least one outer conversion section of the housing of the electrostimulation device may be conductive, and may be connected to one input of an AC voltage converter provided in the signal line. A body contact that is connected to an output of the AC voltage converter provided in the signal line is itself provided on the signal line in particular on or near a distal end thereof. This makes it possible to implement the fact that a line path runs through the tissue of a patient, replacing a line wire or signal line. In traditional pacemakers or implantable defibrillators, which are typically accommodated in a titanium sheet metal housing, the entire housing may form one of the body contacts of the body line path. In an alternative embodiment, the conductive segment is attached to a non-conducting housing of the electrostimulation device.

BRIEF DESCRIPTION OF THE DRAWINGS

Additional advantages and preferred aspects of the present invention are derived from the following description of exemplary embodiments and aspects with reference to the figures, in which.

DETAILED DESCRIPTION OF PREFERRED VERSIONS OF THE INVENTION

Figure 1:
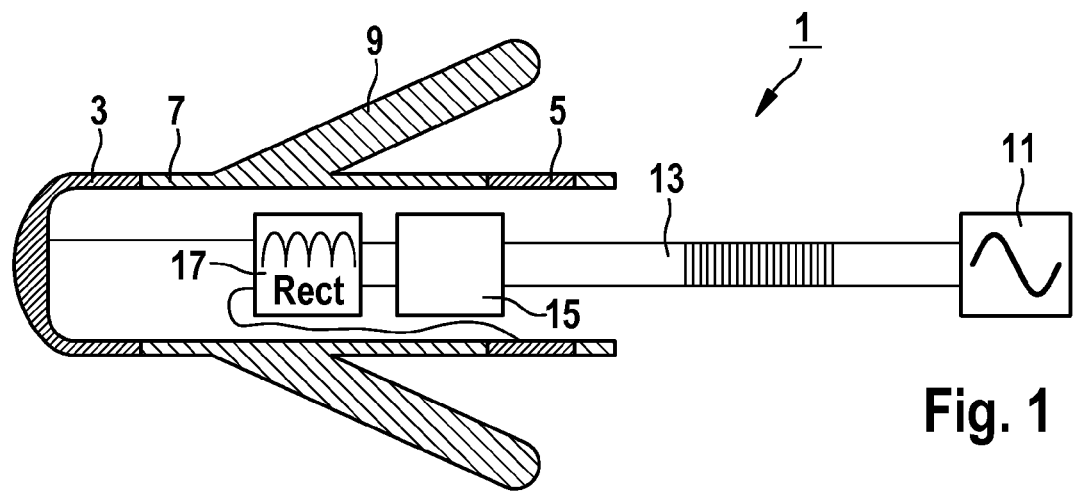
FIG. 1 shows a schematic diagram of a first embodiment of the invention.

FIG. 1 shows schematically the distal end of a pacemaker electrode line 1 with a tip electrode 3 and a ring electrode 5 in an insulating electrode head 7, of which two fins 9 are also shown for anchoring in the trabecular network of the heart. The electrodes 3, 5 receive stimulation pulses here via a mechanical energizer 11 which precedes a mechanical transducer 13 and a mechanoelectric converter 15 that operates on a piezoelectric basis. At the output end of the mechanoelectric converter 15, an AC voltage corresponding to the oscillation frequency of the mechanical energizer 11 is made available and is converted by a rectifier unit 17 into a DC voltage and sent to the tip electrodes 3 and/or the ring electrode 5.

Figure 2:
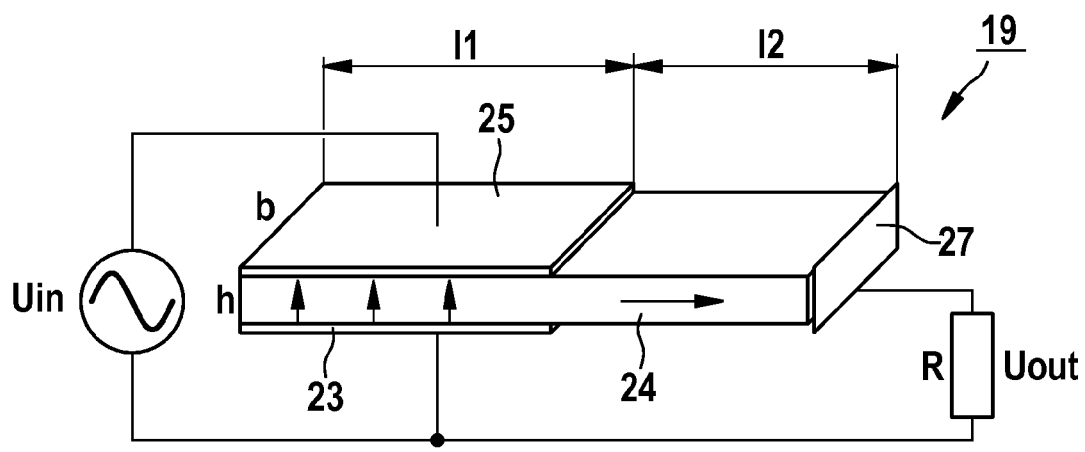
FIG. 2 shows a schematic diagram of a first embodiment of an AC voltage converter to be used in the invention.

FIG. 2 shows schematically a piezoelectric "transformer" 19 that can be used as an AC voltage converter 15 within the scope of the present invention, the main component being a combination piezoelectric element whose direction of polarization and wiring are shown in the figure. The combination piezoelectric element has a length of 11+12, a width b and a height h, and is provided over a portion of its main surfaces with first and second electrodes 23, 25, and with a third electrode 27 on one of its short end faces. An input voltage Uin is applied to the first and second electrodes 23, 25 and an output voltage Uout is picked up via the third electrode 27 and a load resistor R, the amount of said output voltage being determined by the equation Uout/Uin=12/h.

Figure 3:
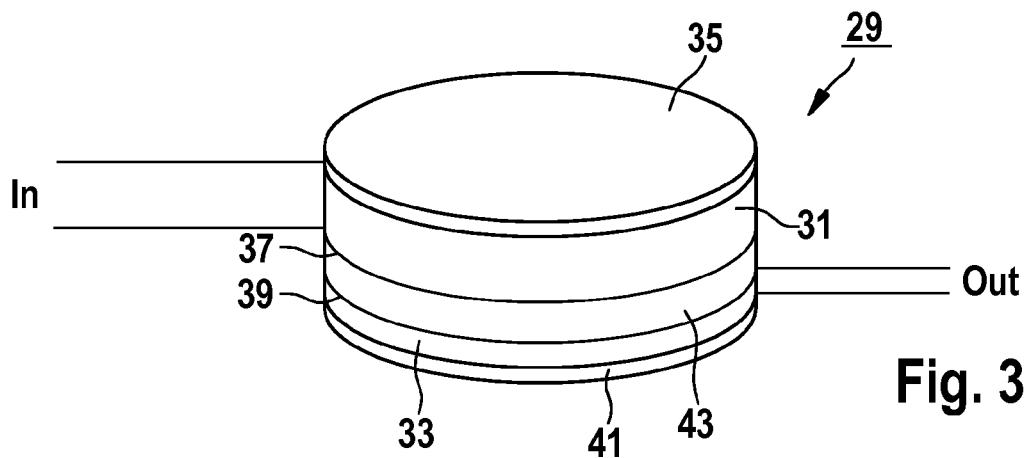
FIG. 3 shows a schematic diagram of a second embodiment of an AC voltage converter to be used in the invention.

FIG. 3 shows schematically another piezoelectric AC voltage converter 29 which operates according to the principle of the four-point transformer. It comprises two flat cylindrical and/or disk-shaped piezoelectric elements 31, 33, which are of different thicknesses and whose end faces are each covered by terminal electrodes 35, 37 and/or 39, 41 and between which an insulating disk 43 is arranged. As with the aforementioned piezoelectric converter 19 that operates by the three-point transformer principle, the geometric parameters of the piezoelectric components determine the Uin/Uout ratio, i.e., the transformation ratio. The output voltage (as described in the embodiment according to FIG. 1) may be rectified prior to its use, e.g., as electrostimulation voltage.

Figure 4:
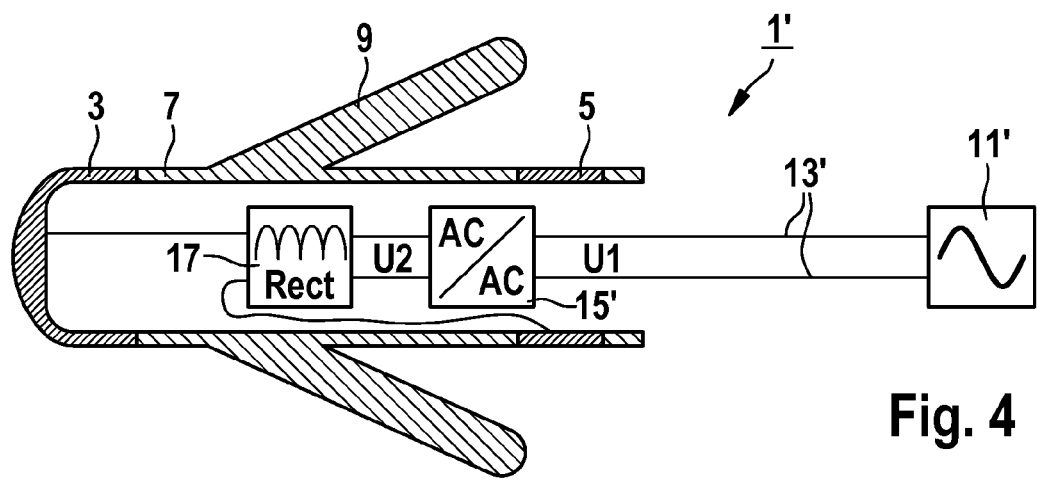
FIG. 4 shows a diagram of another embodiment of the invention.

FIG. 4 illustrates as the second embodiment of the invention a modification of the first embodiment illustrated in FIG. 1, whereby parts having the same or similar functions are labeled with the same reference numerals as in FIG. 1 and are not described again here. The modified electrode line 1' differs from that in FIG. 1 through the presence of a piezoelectric transformer 15' instead of the mechanoelectric converter 15 as well as by an elongated, electrically conductive connection (two-wire line) 13' with a pulse generator 11', which is designed here as an electric generator.

Figure 5:
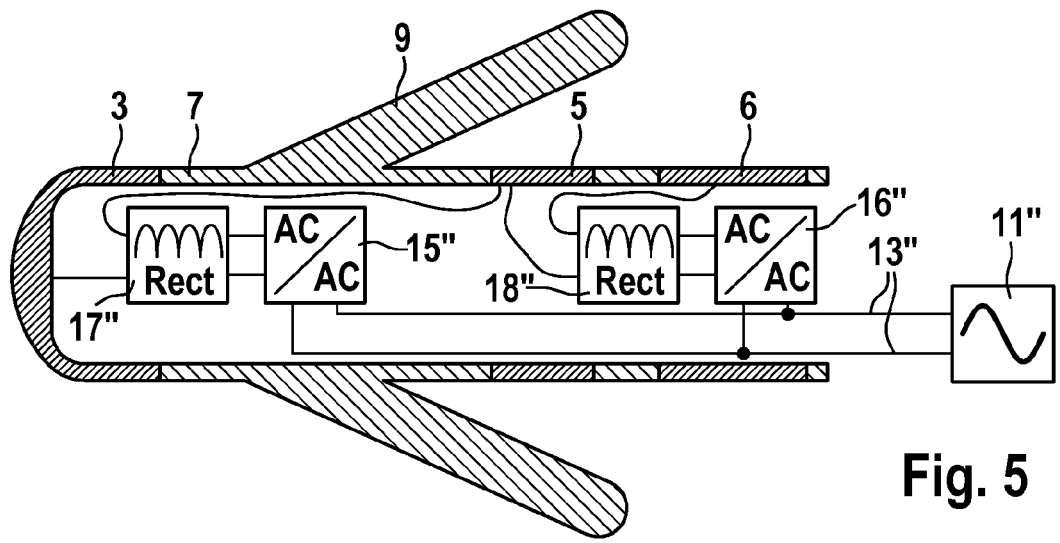
FIG. 5 shows a diagram of yet another embodiment of the invention.

FIG. 5 shows another inventive electrode line 1" that is obtained as an additional modification of the signal line shown in FIG. 4. The electrode head here also has a second ring electrode 6 in addition to the tip electrode 3 and a (first) ring electrode 5 to be able to transmit two different types of stimulation pulses separately to the stimulable tissue of a patient.

The electrode line 1" is connected to an electric generator 11" which supplies two separate output voltages with frequency coding (i.e., applied to different carrier frequencies). Both output voltages of the generator 11" are transmitted jointly on the two-wire line 13' to the electrode head where the electromechanical converters 15" and 16" generate different motion outputs in response to the same input electric AC voltage signal. The input signal is thereby transformed down and rectified by two separate transformer-rectifier units 15"/17" and 16"/18". One output of each of the two rectifier units 16" and 17" is connected to the first ring electrode 5, which serves here as the common reference electrode, while the second output of the rectifier 17" is connected to the tip electrode 3 and the second output of the rectifier 18" is connected to the second ring electrode 6.

The embodiments according to FIGS. 4 and 5 offer the advantage that a higher voltage than would be appropriate for stimulation of the tissue can be supplied to each respective electrode line: due to the AC voltage converter provided close to the distal end of the line, there is a transformation down to the required stimulation voltage. This allows the use of higher-resistance line wires within the electrode line, which may in turn produce a reduction in the thickness and stiffness and also increase the resistance to EMI interference. The embodiment illustrated in FIG. 5 also has the advantage that only a single line pair is required for conducting the various output voltages of the stimulation pulse generator, and the structural expense, thickness and stiffness can be reduced significantly in comparison with known electrode lines having the same function.

Figure 6:
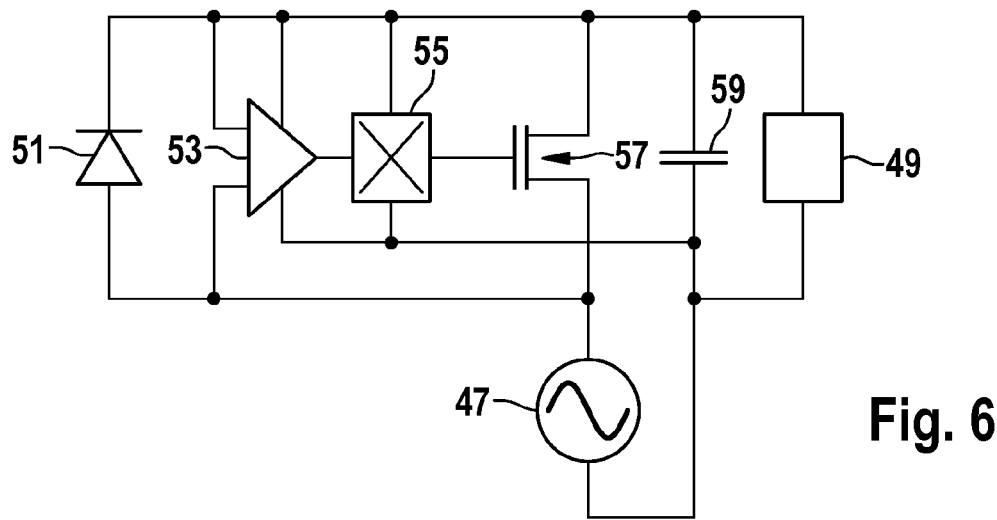
FIG. 6 shows a schematic diagram of an active rectifier unit which may be used within the scope of the invention.

FIG. 6 shows a schematic diagram of an active rectifier unit 45 that can be used as part of the invention (e.g., at 17, 17' and 17" in FIGS. 1, 4, and 5), connected following an AC voltage converter (e.g., at 15, 15', 15" and 16" in FIGS. 1, 4, and 5). The symbol of an AC voltage generator here is used to symbolize an AC voltage converter 47, and the circuit comprises, e.g., a stimulation electrode, a diode 51, a voltage comparator 53, a voltage multiplier 55, a switching transistor 57 and a buffer capacitor 59 in the circuit shown here for connection to a load 49. The AC voltage generator (AC/AC converter) 47 generates an alternating voltage in the forward direction of the diode 51.

The circuit functions as follows: the AC voltage generator 47 generates an alternating voltage in the forward direction of the diode 51. Until reaching the forward voltage, a voltage difference that builds up across the diode 51 is recorded by the voltage comparator 53 and amplified and switches the switching transistor 57 that bridges the diode 51. The power for supplying the active elements is supplied by the buffer capacitor 59, which is operated in parallel with the load 49. As soon as the capacitor 59 is empty, rectification is initially passive until the capacitor 59 is charged up enough to supply the active part of the circuit.

A full-wave rectifier can be created by using multiple active switches and voltage comparators. The voltage comparator may include a differential element to also react to the steepness of a signal and not just its amplitude.

In another modification of this active rectifier unit, it is possible to have the voltage comparator connected upstream from the AC voltage converter (transformer) rather than being connected downstream from it. This offers the advantage that the signal modulation is greater at this point and the rising flank of the signal is steeper.

Figure 7:
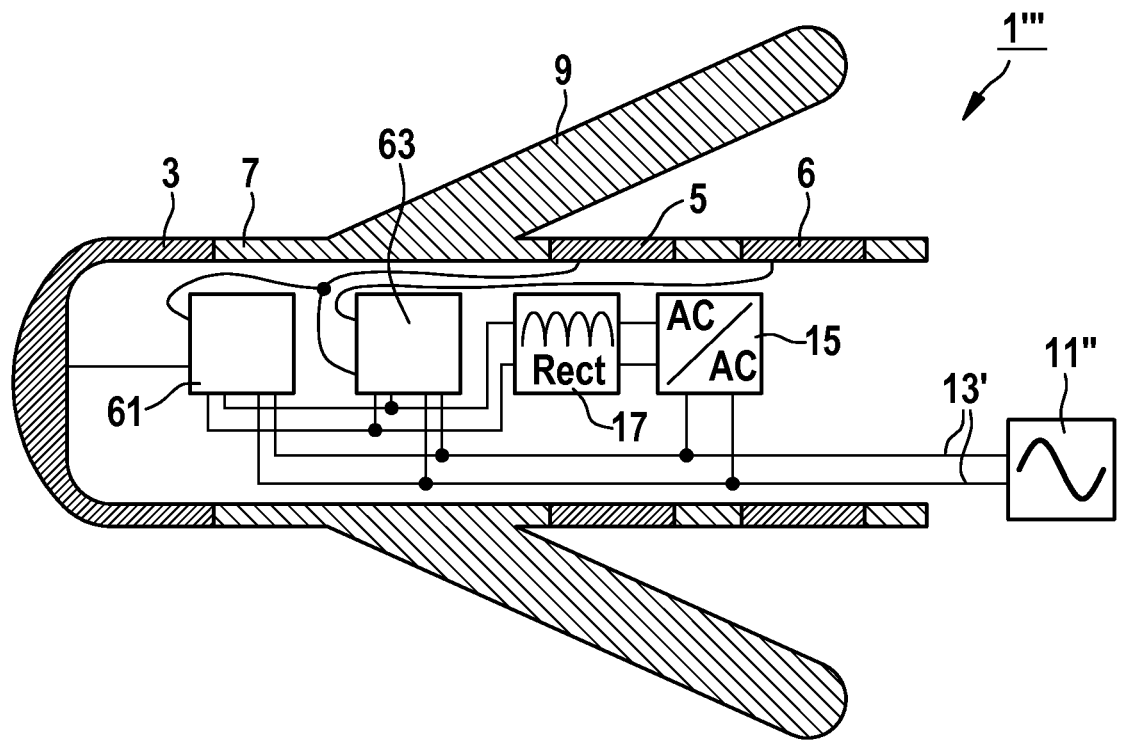
FIG. 7 shows a diagram of yet another embodiment of the invention.

FIG. 7 shows an electrode line 1''' as another modification of the embodiment illustrated in FIG. 5 and described above. The reference numerals for the same or equivalent parts are labeled here like those in FIG. 5. Instead of two transformer-rectifier combinations, a single transformer-rectifier unit 15/17 is provided here in combination with two frequency-controlled switches 61, 63, which operate at different frequencies and both of which are supplied over the single two-wire line 13'. A selected energizing voltage may be applied selectively to the electrode pairs 3/5 and/or 3/6 via the frequency-controlled switches 61, 63.

Figure 8:
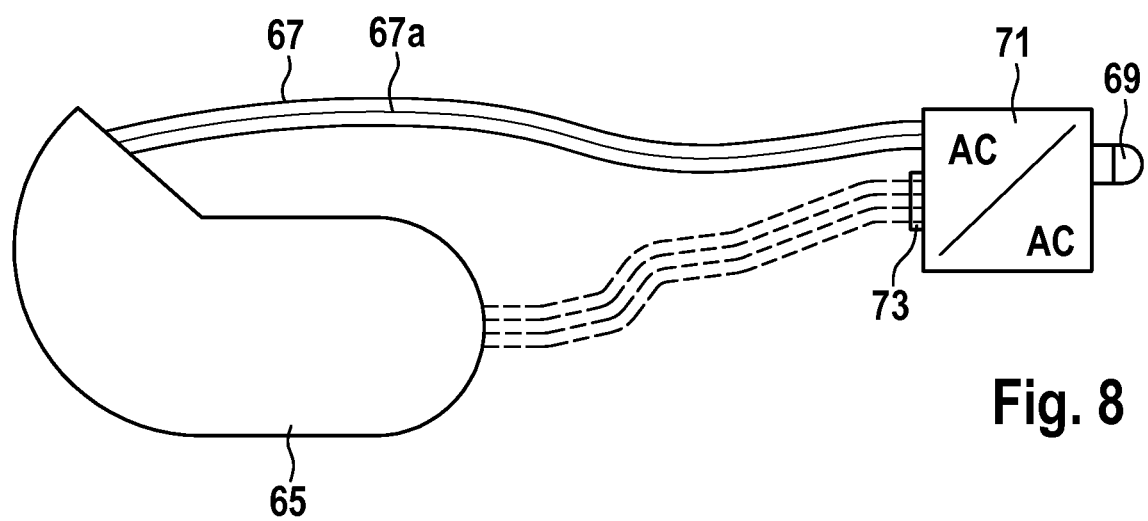
FIG. 8 shows a schematic diagram of an expedient embodiment of an inventive configuration with an electrostimulation device.

FIG. 8 shows a schematic diagram of one embodiment of an inventive configuration of a heart pacemaker 65 (as an example of an implantable basic device), an electrode line 67 with a stimulation electrode 69 on the distal end, and an AC voltage converter 71 preceding the stimulation electrode 69. The housing of the pacemaker 65 is made of sheet metal (as usual) and thus represents a first body contact of the overall configuration to which one pole of the (AC voltage) generator (not shown in the figure but provided in the housing of pacemaker 65) is connected.

A body contact 73 is likewise provided on the AC voltage converter 71 close to the end of the electrode line 67 and is connected to the converter input. Between the housing of the pacemaker 65 and the second body contact 73 a "body conduction path" is formed, which, together with a line wire 67a within the electrode line 67, closes the circuit between the pulse generator and the AC voltage converter.

This makes it possible to omit one line wire of the usual two-wire line within the electrode line. In particular, a piezoelectric transformer can be controlled with only one line wire in the electrode line. If the signals are transmitted with frequency coding, as already mentioned above, then multiple effective voltages and/or channels may also be transmitted over the one-line wire in the electrode line (each utilizing the body conduction path) and the line wire savings become even more greater.

With a basic device having a non-conducting housing, conducting sections which serve as a device-side body contact may also be provided on the housing, as a modification of the last embodiment mentioned above.

The invention is not limited to the examples mentioned above and aspects emphasized herein, but instead is also possible in a variety of modified embodiments within the scope of protection of the accompanying claims.

What is claimed is:

1. An electrical configuration for an electromedical device including:
   a. stimulation electrodes situated externally on or from the electromedical device;
   b. an input electric line bearing an input electric AC voltage signal;
   c. an AC voltage converter receiving the input electric AC voltage signal and producing output electric AC voltage signals therefrom, the AC voltage converter including:
      (1) two or more electromechanical converters, each electromechanical converter receiving at least a portion of the input electric AC voltage signal and converting it into a motion, wherein at least a portion of the output electric AC voltage signals are subsequently generated from the motion, and
      (2) two or more mechanoelectric converters, each mechanoelectric converter converting motion into one of the output electric AC voltage signals,
   wherein:
      i. the AC voltage converter is provided as a unit situated within an electrode line, and
      ii. different ones of the stimulation electrodes are supplied with different output electric AC voltage signals from different respective ones of the mechanoelectric converters.

2. The electrical configuration of claim 1 wherein at least two of the electromechanical converters generate different motion outputs in response to the same input electric AC voltage signal.

3. The electrical configuration of claim 1 wherein the mechanoelectric converters generate at least two output electric AC voltage signals having different voltages.

4. The electrical configuration of claim 1 wherein each mechanoelectric converter is connected following a respective one of the electromechanical converters.

5. The electrical configuration of claim 1 wherein the electromechanical converters and the mechanoelectric converters are adjacently situated within the electrode line.

6. The electrical configuration of claim 1 further including an output electric line from the AC voltage converter, wherein the output electric line has a lower resistance than the input electric line.

7. The electrical configuration of claim 1 wherein a piezoelectric element is provided within any electromechanical converter and/or mechanoelectric converter within the AC voltage converter.

8. The electrical configuration of claim 1 wherein the AC voltage converter includes a piezoelectric element having:
   a. opposing first and second electrodes on opposing surfaces of the piezoelectric element, and
   b. a third electrode on a surface oriented at least substantially perpendicular to one or more of the first and second electrodes.

9. The electrical configuration of claim 1 wherein the AC voltage converter includes multiple electrodes with piezoelectric elements sandwiched between pairs of the electrodes.

10. The electrical configuration of claim 1 wherein one or more frequency-controlled switches are connected following one of the mechanoelectric converters, each switch:
    a. passing at least a portion of the output electric AC voltage signals if the input electric AC voltage signal is at one or more acceptable frequencies, and
    b. otherwise blocking the output electric AC voltage signals.

11. The electrical configuration of claim 1 wherein:
    a. the electrode line extends from a housing, at least a portion of the housing being electrically conductive, wherein the electrically conductive portion of the housing is connected in conductive communication with the input electric line; and
    b. a body contact situated externally on or from the electromedical device receives at least a portion of the input electric AC voltage signal.

12. The electrical configuration of claim 1 further including a rectifier receiving at least a portion of one of the output electric AC voltage signals.

13. The electrical configuration of claim 1 wherein each stimulation electrode's voltage signal is rectified prior to reaching the stimulation electrode.

\* \* \* \* \*